(12) United States Patent
Amling

(10) Patent No.: US 9,687,140 B2
(45) Date of Patent: *Jun. 27, 2017

(54) AUTO ZOOM FOR VIDEO CAMERA

(71) Applicant: Marc R. Amling, Santa Barbara, CA (US)

(72) Inventor: Marc R. Amling, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 151 days.

This patent is subject to a terminal disclaimer.

(21) Appl. No.: 14/744,102

(22) Filed: Jun. 19, 2015

(65) Prior Publication Data

US 2015/0282691 A1    Oct. 8, 2015

Related U.S. Application Data

(63) Continuation of application No. 13/649,871, filed on Oct. 11, 2012, now Pat. No. 9,060,674.

(51) Int. Cl.
| | |
|---|---|
| *A61B 1/04* | (2006.01) |
| *A61B 1/00* | (2006.01) |
| *A61B 1/045* | (2006.01) |
| *H04N 5/262* | (2006.01) |
| *G06T 3/00* | (2006.01) |

(Continued)

(52) U.S. Cl.
CPC .......... *A61B 1/00045* (2013.01); *A61B 1/005* (2013.01); *A61B 1/00009* (2013.01); *A61B 1/00011* (2013.01); *A61B 1/00039* (2013.01); *A61B 1/00078* (2013.01); *A61B 1/042* (2013.01); *A61B 1/045* (2013.01); *A61B 1/05* (2013.01); *A61B 1/0661* (2013.01); *G06T 3/00* (2013.01); *H04N 5/23296* (2013.01); *H04N 5/2628* (2013.01); *H04N 2005/2255* (2013.01)

(58) Field of Classification Search
CPC ............ A61B 1/00009; A61B 1/00043; A61B 1/00045; A61B 1/045; H04N 5/2628; H04N 5/23296
USPC ................................................. 600/118, 168
See application file for complete search history.

(56) References Cited

U.S. PATENT DOCUMENTS

| | | |
|---|---|---|
| 3,817,635 A | 6/1974 | Kawahara |
| 3,856,000 A | 12/1974 | Chikama |

(Continued)

FOREIGN PATENT DOCUMENTS

| | | |
|---|---|---|
| EP | 1929933 A2 | 6/2008 |
| EP | 1972260 A1 | 9/2008 |

OTHER PUBLICATIONS

European Search Report Application No. EP 13 18 8094 Completed: Jan. 17, 2014; Mailing Date: Jan. 27, 2014 6 pages.

(Continued)

*Primary Examiner* — John P Leubecker
(74) *Attorney, Agent, or Firm* — Whitmyer IP Group LLC

(57) ABSTRACT

An endoscope, endoscopic system and method for filling a medical display with a medical image involving sizing the medical image so that it covers at least one of the dimensions of the medical display. Automatically sizing the medical image to fit either the vertical, horizontal, or corner-to-corner dimensions of the surgical display, the sizing of the image involving adjusting the image size to account for changing zoom factors, endoscopes and imaging conditions.

22 Claims, 6 Drawing Sheets

(51) Int. Cl.
*H04N 5/232* (2006.01)
*A61B 1/005* (2006.01)
*A61B 1/05* (2006.01)
*A61B 1/06* (2006.01)
*H04N 5/225* (2006.01)

(56) References Cited

U.S. PATENT DOCUMENTS

| | | |
|---|---|---|
| 4,277,168 A | 7/1981 | Oku |
| 4,355,330 A | 10/1982 | Fukui |
| 4,432,014 A | 2/1984 | Roos et al. |
| 4,488,039 A | 12/1984 | Sato et al. |
| 4,491,865 A | 1/1985 | Danna et al. |
| 4,527,201 A | 7/1985 | Cappels |
| 4,558,691 A | 12/1985 | Okada |
| 4,570,185 A | 2/1986 | Arai et al. |
| 4,692,608 A | 9/1987 | Cooper et al. |
| 4,765,313 A | 8/1988 | Kumakura |
| 4,777,524 A | 10/1988 | Nakajima et al. |
| 4,781,448 A | 11/1988 | Chatenever et al. |
| 4,832,003 A | 5/1989 | Yabe |
| 4,846,155 A | 7/1989 | Kimura |
| 4,867,137 A | 9/1989 | Takahashi |
| 4,868,645 A | 9/1989 | Kobayashi |
| 4,891,697 A | 1/1990 | Saito et al. |
| 4,950,054 A | 8/1990 | Wada et al. |
| 4,989,253 A | 1/1991 | Liang et al. |
| 5,122,650 A | 6/1992 | McKinley |
| 5,144,492 A | 9/1992 | Iijima et al. |
| 5,187,776 A | 2/1993 | Yanker |
| 5,216,512 A | 6/1993 | Bruijns et al. |
| 5,228,430 A | 7/1993 | Sakamoto |
| 5,261,404 A | 11/1993 | Mick et al. |
| 5,418,645 A | 5/1995 | Coath et al. |
| 5,475,426 A | 12/1995 | Kinugasa et al. |
| 5,491,527 A | 2/1996 | Oshikiri et al. |
| 5,503,320 A | 4/1996 | Webster et al. |
| 5,506,912 A | 4/1996 | Nagasaki et al. |
| 5,552,605 A | 9/1996 | Arata |
| 5,572,999 A | 11/1996 | Funda et al. |
| 5,582,576 A | 12/1996 | Hori et al. |
| 5,662,584 A | 9/1997 | Hori et al. |
| 5,815,640 A | 9/1998 | Wang et al. |
| 5,817,014 A | 10/1998 | Hori et al. |
| 5,836,869 A | 11/1998 | Kudo et al. |
| 5,876,325 A | 3/1999 | Mizuno et al. |
| 5,910,801 A | 6/1999 | Rosenburg et al. |
| 5,945,985 A | 8/1999 | Babin et al. |
| 5,989,182 A | 11/1999 | Hori et al. |
| 6,117,071 A | 9/2000 | Ito et al. |
| 6,221,014 B1 | 4/2001 | Bauer |
| 6,224,542 B1 | 5/2001 | Chang et al. |
| 6,262,763 B1 | 7/2001 | Totsuka et al. |
| 6,277,067 B1 | 8/2001 | Blair |
| RE37,356 E | 9/2001 | Hori et al. |
| 6,329,998 B1 | 12/2001 | Han |
| 6,339,434 B1 | 1/2002 | West et al. |
| 6,389,176 B1 | 5/2002 | Hsu et al. |
| 6,392,816 B1 | 5/2002 | Hamano |
| 6,397,286 B1 | 5/2002 | Chatenever et al. |
| 6,402,685 B1 | 6/2002 | Igarashi |
| 6,422,995 B2 | 7/2002 | Akiba |
| 6,437,925 B1 | 8/2002 | Nishioka |
| 6,447,447 B1 | 9/2002 | Mitsumori |
| 6,450,949 B1 | 9/2002 | Farkas et al. |
| 6,464,363 B1 | 10/2002 | Nishioka et al. |
| 6,478,730 B1 | 11/2002 | Bala et al. |
| 6,491,628 B1 | 12/2002 | Kobayashi |
| 6,508,760 B2 | 1/2003 | Yamanaka et al. |
| 6,527,732 B1 | 3/2003 | Strauss et al. |
| 6,533,721 B1 | 3/2003 | Beutter et al. |
| 6,537,208 B1 | 3/2003 | Konno |
| 6,572,539 B2 | 6/2003 | Akiba |
| 6,591,239 B1 | 7/2003 | McCall et al. |
| 6,613,056 B1 | 9/2003 | Brumbach et al. |
| 6,618,209 B2 | 9/2003 | Nishioka et al. |
| 6,642,836 B1 | 11/2003 | Wang et al. |
| 6,648,816 B2 | 11/2003 | Irion et al. |
| 6,674,439 B1 | 1/2004 | Shin et al. |
| 6,712,760 B2 | 3/2004 | Sano et al. |
| 6,738,199 B2 | 5/2004 | Nishioka |
| 6,743,168 B2 | 6/2004 | Luloh et al. |
| 6,749,561 B2 | 6/2004 | Kazakevich |
| 6,767,321 B2 | 7/2004 | Czarnek et al. |
| 6,771,417 B1 | 8/2004 | Wolleschensky et al. |
| 6,791,741 B2 | 9/2004 | Hishioka |
| 6,801,370 B2 | 10/2004 | Sekiyama et al. |
| 6,806,899 B1 | 10/2004 | Schaack |
| 6,814,699 B2 | 11/2004 | Ross et al. |
| 6,865,009 B2 | 3/2005 | Nishioka |
| 6,869,397 B2 | 3/2005 | Black et al. |
| 6,911,916 B1 | 6/2005 | Wang et al. |
| 6,919,914 B2 | 7/2005 | Beutter et al. |
| 6,930,705 B2 | 8/2005 | Tanaka |
| 6,932,762 B2 | 8/2005 | Ayame et al. |
| 6,943,663 B2 | 9/2005 | Wang et al. |
| 7,008,416 B2 | 3/2006 | Sakaguchi et al. |
| 7,010,223 B2 | 3/2006 | Thoms |
| 7,019,919 B2 | 3/2006 | Wakai et al. |
| 7,022,118 B2 | 4/2006 | Ariura et al. |
| 7,053,752 B2 | 5/2006 | Wang et al. |
| 7,057,639 B2 | 6/2006 | Spoonhower et al. |
| 7,095,401 B2 | 8/2006 | Liu et al. |
| 7,097,640 B2 | 8/2006 | Wang et al. |
| 7,108,687 B2 | 9/2006 | Furukawa |
| 7,136,098 B1 | 11/2006 | Burnett et al. |
| 7,137,948 B2 | 11/2006 | Tsai |
| 7,259,652 B2 | 8/2007 | Wang et al. |
| 7,259,906 B1 | 8/2007 | Islam |
| 7,269,344 B2 | 9/2007 | Nishioka et al. |
| 7,319,962 B2 | 1/2008 | Goedeke et al. |
| 7,362,894 B2 | 4/2008 | Ono et al. |
| 7,375,311 B2 | 5/2008 | Wiklof et al. |
| 7,395,249 B2 | 7/2008 | Wang et al. |
| 7,408,439 B2 | 8/2008 | Wang et al. |
| 7,433,116 B1 | 10/2008 | Islam |
| 7,450,154 B2 | 11/2008 | Kojima et al. |
| 7,543,588 B2 | 6/2009 | Wang et al. |
| 7,601,119 B2 | 10/2009 | Shahinian |
| 7,608,039 B1 | 10/2009 | Todd |
| 7,633,673 B1 | 12/2009 | Islam |
| 7,664,383 B2 | 2/2010 | Nilsson |
| 7,672,849 B2 | 3/2010 | Yudkovitch et al. |
| 7,714,885 B2 | 5/2010 | Yazawa et al. |
| 7,733,584 B2 | 6/2010 | Kazakevich |
| 7,734,160 B2 | 6/2010 | Sudo et al. |
| 7,738,684 B2 | 6/2010 | Kariathungal et al. |
| 7,769,280 B2 | 8/2010 | Vogeli |
| 7,824,328 B2 | 11/2010 | Gattani et al. |
| 7,852,371 B2 | 12/2010 | Konstorum et al. |
| 7,855,727 B2 | 12/2010 | Adler et al. |
| 7,872,816 B2 | 1/2011 | Chen et al. |
| 7,892,168 B2 | 2/2011 | Sano |
| 7,907,168 B2 | 3/2011 | Eino |
| 7,914,444 B2 | 3/2011 | Moriyama et al. |
| 7,914,447 B2 * | 3/2011 | Kanai ............... G02B 21/0028 348/68 |
| 7,935,108 B2 | 5/2011 | Baxter et al. |
| 7,961,401 B1 | 6/2011 | Scott et al. |
| 7,978,891 B2 | 7/2011 | Assmann et al. |
| 8,016,751 B2 | 9/2011 | Weigel et al. |
| 8,016,754 B2 | 9/2011 | Takahashi |
| 8,026,942 B2 | 9/2011 | Payonk et al. |
| 8,033,990 B2 | 10/2011 | Otawara |
| 8,055,108 B2 | 11/2011 | Islam |
| 8,075,479 B2 | 12/2011 | Takahashi |
| 8,079,950 B2 | 12/2011 | Stern et al. |
| 8,081,186 B2 | 12/2011 | Wong et al. |
| 8,098,423 B2 | 1/2012 | Islam |
| 8,373,748 B2 | 2/2013 | Pang et al. |
| 2002/0101646 A1 | 8/2002 | Ide et al. |
| 2003/0200119 A1 | 10/2003 | Lewis et al. |
| 2003/0215120 A1 | 11/2003 | Uppaluri et al. |
| 2004/0068167 A1 | 4/2004 | Hsieh et al. |

(56) References Cited

U.S. PATENT DOCUMENTS

| | | |
|---|---|---|
| 2004/0169668 A1 | 9/2004 | Yamada et al. |
| 2004/0190154 A1 | 9/2004 | Wakai et al. |
| 2005/0093972 A1 | 5/2005 | Higuchi |
| 2005/0102315 A1 | 5/2005 | Krishnan |
| 2005/0228250 A1 | 10/2005 | Bitter et al. |
| 2005/0288553 A1 | 12/2005 | Sugimoto |
| 2006/0133658 A1 | 6/2006 | Spahn |
| 2006/0139318 A1 | 6/2006 | Kariathungal et al. |
| 2007/0025606 A1 | 2/2007 | Gholap et al. |
| 2007/0036405 A1 | 2/2007 | Lienard et al. |
| 2007/0154075 A1 | 7/2007 | Matsumoto |
| 2007/0274587 A1 | 11/2007 | Eronen |

OTHER PUBLICATIONS

European Office Action Application No. 13188094.0 Issued: Apr. 5, 2016 4 Pages.

* cited by examiner

Endoscopic Image - Typical

Endoscopic Image Vertically Optimized

Endoscopic Image
Horizontally Optimized

Endoscopic Image
Corner-to-Corner Optimized

AUTO ZOOM FOR VIDEO CAMERA

FIELD OF THE INVENTION

The present invention relates to a system and method for filling a medical display with a medical image.

BACKGROUND OF THE INVENTION

Endoscopes and endoscopic systems include cameras and other imaging modules that provide images on a medical display. These images can be viewed by surgeons and nurses during a surgical procedure. Typically, endoscopes and endoscopic systems do not allow surgeons to have a direct view of the surgical area during a surgical procedure and rely on cameras and imagers to transmit an image of the surgical area to a medical display.

Endoscopes in the art may be rigid or flexible. For rigid endoscopes coupled to proximal camera systems, the endoscopic image size (size of the endoscope mask) relative to the medical display size is typically determined by the diameter of the rod lens system in the endoscope and the magnification of the optics.

To facilitate coupling endoscopes having various diameters with medical displays having different dimensions, camera systems and imagers are provided with either optical or digital zoom, so that the medical image provided by the endoscope imagers can be adjusted to fit a medical display.

Users, such as surgeons or nurses, can manually optimize the image size transmitted from the endoscope on the surgical display, so that the endoscopic image is optimized for the medical display. However, optimization using both optical and digital zoom is a user intervention limitation that is performed manually. This means that a person, such as surgeon or nurse, has to manually adjust the optical or digital zoom of the endoscope so that the medical image appears properly and is optimized on the display. Being optimized means that the image is properly framed (sized) for the endoscopic display.

This manual intervention is disadvantageous as the user has to turn a knob, press a button or possibly adjust a camera imager, so as to manually adjust the optical and/or digital zoom so that the medical image appears properly sized for the display.

Known prior art includes U.S. Pat. No. 4,488,039 Sato et al.; U.S. Pat. No. 5,506,912 Nagasaki et al.; U.S. Pat. No. 4,570,185 Arai et al.; U.S. Pat. No. 5,582,576 Hori et al.; U.S. Pat. No. 4,781,448 Chatenever et al.; U.S. Pat. No. 5,662,584 Hori et al.; U.S. Pat. No. 4,891,697 Saito et al. al.; U.S. Pat. No. 5,910,801 Rosenburg et al.; and U.S. Pat. No. 5,144,492 Iijima et al. These references all involve manual intervention for optimizing images.

None of these references discloses automatically adjusting the optical and/or digital zoom so as to optimize the medical image, so the medical image appears properly on the display.

None of these references disclose using gesture detection or voice control to adjust the optical and/or digital zoom so as to optimize the medical image, so the medical image appears properly on the display.

Thus, it is desirable to provide an endoscope, endoscopic surgical system and method that automatically adjusts the optical and/or digital zoom so as to optimize the medical image, so that the medical image appears properly on the display.

It is also desirable to provide an endoscope, endoscopic surgical system and method using gesture detection or voice control to adjust the optical or digital zoom so as to optimize the medical image, so that the medical image appears properly on the display.

The endoscope, endoscopic surgical system and method provide the ability for surgeons, nurses, and/or other people in an operating room to optimize the medical image, so that the medical image appears properly on the display, which leads to optimized viewing of the medical images during a surgical procedure.

SUMMARY OF THE INVENTION

Accordingly, it is an object of the present invention to provide an endoscope, endoscopic surgical system and method that automatically adjusts the optical and/or digital zoom so as to optimize the medical image, so that the medical image appears properly sized on the display.

It is another object of the present invention to provide an endoscope, endoscopic surgical system and method that uses gesture detection and/or voice control to adjust the optical or digital zoom so as to optimize the medical image, so that the medical image appears properly sized on the display.

These and other objects of the invention are achieved by providing a method for filling a medical display with a medical image, the method comprising: providing a medical display, the medical display having two dimensions for displaying an image; receiving the medical image; and sizing the medical image, so that it covers at least one of the dimensions of the medical display.

In certain embodiments, the image is vertically optimized, horizontally optimized or corner-to-corner optimized in the medical display. In certain embodiments, the image is optimized in the medical display, so that it is substantially optimized vertically, horizontally or corner-to-corner, and includes almost all of the display. In certain embodiments, the image is optimized according to some other predetermined size. In certain embodiments, the two dimensions of the medical display includes pixels to display the image. In other embodiments, the medical display includes various other electronic elements that may display an image including liquid crystal technology or plasma technology.

In certain embodiments, a user can select a region of interest in the medical display before and after the image has been optimized. In certain embodiments, the user can further optimize the selected region of interest using voice control or gesture detection. In certain embodiments, the user can optimized the selected region of interest using other control methods.

In certain embodiments, the sizing of the image is automatic. In certain embodiments, the sizing the image is controlled by gesture detection or voice control. In certain embodiments, the sizing of the image is via other control methods.

In certain embodiments, the selected region of interest can be automatically optimized via gesture detection or voice control. In certain embodiments, the selected region of interest can be automatically optimized via other control methods.

In certain embodiments, the image is a medical image and is received from an imager, such as a solid state imager. In certain embodiments, the method includes determining the size of the medical display and the corresponding zoom factor to either fill the surgical display vertically, horizontally or corner-to-corner.

In certain embodiments, the method includes determining the black circular mask or pixels that do not have a medical image. The method may calculate the percentage of the screen that does not include the image and size the image in this manner. In certain embodiments, the method may calculate the horizontal and/or vertical dimensions of the screen that does not include the image and size the image to optimize the horizontal and/or vertical dimensions.

In certain embodiments, the sizing of the image accounts for changing zoom factors, various endoscopes that are used, and imaging conditions.

Other objects of the invention are achieved by providing a method for sizing an endoscopic image to fit a display comprising: providing an endoscope, the endoscope associated with an imager; capturing an image with the imager; providing a display in communication with the imager; conveying the image from the imager to the display; and sizing the image to fit the dimensions of the display.

In certain embodiments, the dimensions of the display consist of the vertical, horizontal, or corner-to-corner dimensions of the display. In certain embodiments, the imager is located within the endoscope.

In certain embodiments, the sizing of the image is automatic. In certain embodiments, the sizing of the image involves automatically calculating the size of the medical display and adjusting the size of the medical image to fit the medical display. In certain embodiments, the imager includes zoom factors and the sizing of the image accounts for the zoom factors of the imager.

In certain embodiments, the sizing of the image accounts for the type of imager and the type of endoscope used to capture the image. In certain embodiments, the sizing of the image accounts for imaging conditions. In certain embodiments, the type of imager may be a solid state imager. In certain embodiments, the endoscope may be a flexible endoscope. In certain embodiments, the endoscope may be a rigid endoscope.

In certain embodiments, the sizing of the image involves determining the size of an image corresponding zoom factor associated with the image. The corresponding zoom factor may be 1×, 2×, 3×, 10×, 20×, 50× or other such zoom factors used in the art.

In certain embodiments, the method further comprises image navigation software in communication with the imager. In certain embodiments, the method is performed on an endoscopic video system, CCU, proximal camera or flexible videoscope. In certain embodiments, the method is performed on a distal imager on a rigid endoscope, a distal imager on a flexible endoscope, a videoscope, and endoscope with an embedded imager, the endoscope being either flexible or rigid.

In certain embodiments, the sending of the image from the imager to the display involves sending an electronic signal. In certain embodiments, the sizing of the image to fit the dimensions of the display involves software executing on the display. In certain embodiments, there is a step of processing the image prior to sizing the image.

In certain embodiments, the method further comprises resizing the image to account for changing zoom factors, endoscopes and imaging conditions. In certain embodiments, the resizing of the image involves first determining the original size of the image transmitted to the display. The original size of the image is the size of the image captured by the camera, such as a 12.1 megapixel camera.

In certain embodiments, the method further includes steps of selecting a region of interest. In certain embodiments, the method involves using gesture detection and/or voice control. In certain embodiments, the method involves using other control methods.

Other objects of the invention are achieved by providing an endoscopic surgical system comprising: an endoscope, the endoscope comprising: a housing having an imaging module, an objective lens disposed in the imaging module, an imager disposed in the imaging module, a light source, and a camera control unit in communication with the imaging module, the camera control unit including image navigation software in communication with the imager; a display; and software executing on the display for automatically sizing an endoscope image to fit the dimensions of the display.

In certain embodiments, the dimensions of the display consist of the vertical, horizontal, or corner-to-corner dimensions of the display.

In certain embodiments, the housing has a proximal end and a distal end and a longitudinal axis spanning the proximal end and the distal end.

In certain embodiments, the imager is disposed in the distal end of the housing. In certain embodiments, the imager is disposed in the middle of the housing. In certain embodiments, the light source is disposed in the distal end of the housing. In certain embodiments, the objective lens is disposed in the distal end of the housing.

In certain embodiments, the imager captures a field of view.

In certain embodiments, the objective lens is a wide-angle lens. In certain embodiments, the software for sizing an endoscope image involves sizing the image to fit either the vertical, horizontal, or corner-to-corner dimensions of the display.

In certain embodiments, the software for sizing an endoscope image accounts for changing zoom factors, endoscopes and imaging conditions. In certain embodiments, the software for sizing the image accounts for the type of imager and the type of endoscope used to capture the image. In certain embodiments, the software for sizing the image accounts for imaging conditions.

Other objects of the invention are achieved by providing a method for sizing an endoscopic image to fit a surgical display comprising: providing an imager; capturing an image with the imager; conveying the captured image from the imager to a surgical display in communication with the imager; automatically sizing the captured image to fit either the vertical, horizontal, or corner-to-corner dimensions of the surgical display, the sizing of the image involving adjusting the image size to account for changing zoom factors, endoscopes and imaging conditions.

In certain embodiments, automatically sizing the captured image accounts for magnification factors used to capture the captured image.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what is presently believed to be the best mode of carrying out the invention.

The present invention is directed to providing a novel, unique endoscope, endoscopic surgical system and method that automatically adjusts the optical and/or digital zoom so as to optimize the medical image, so that the medical image appears properly on the display.

Figure 1:
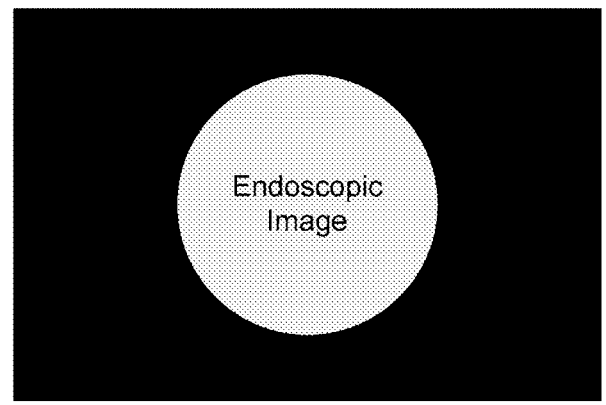
FIG. 1 is a view of an endoscopic image in a medical display of the prior art.

The present invention is also directed to providing a novel, unique endoscope, endoscopic surgical system and method that uses gesture detection or voice control to adjust the optical and/or digital zoom so as to optimize the medical image, so that the medical image appears properly on the display FIG. 1 shows an endoscopic image in the prior art that is not optimized to fully cover the dimensions of the medical display.

Figure 2:
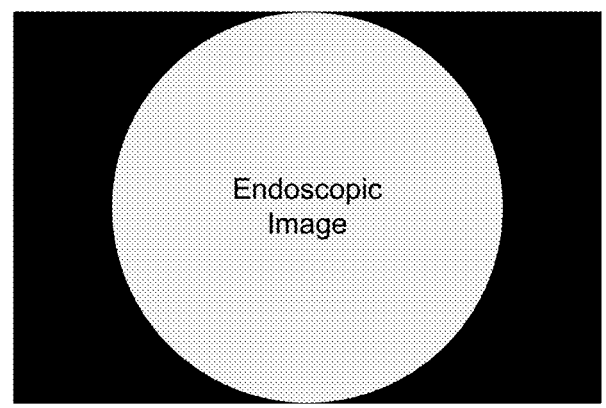
FIG. 2 is a view of an endoscopic image in a medical display that is vertically optimized.

FIG. 2 shows an endoscopic image of an embodiment of the invention where the endoscopic image has been vertically optimized so that it covers the vertical dimension of the medical display.

Figure 3:
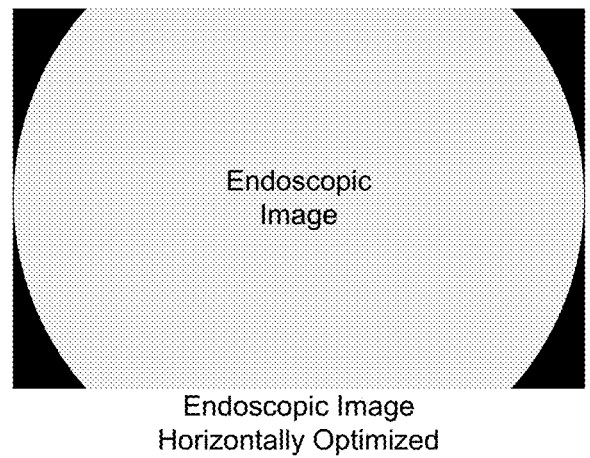
FIG. 3 is a view of an endoscopic image in a medical display that is horizontally optimized.

FIG. 3 shows an endoscopic image of an embodiment of the invention where the endoscopic image has been horizontally optimized so that it covers the horizontal dimension of the medical display.

Figure 4:
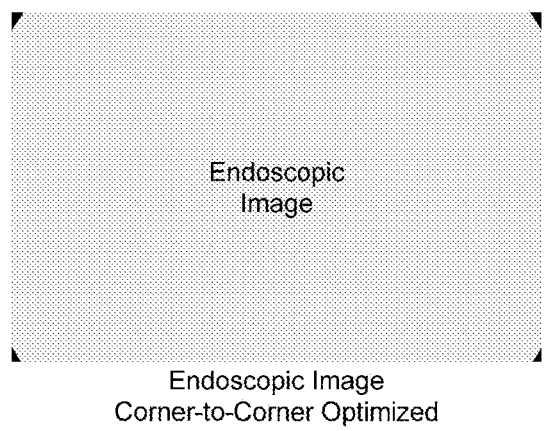
FIG. 4 is a view of an endoscopic image in a medical display that is corner-to-corner optimized.

FIG. 4 shows an endoscopic image of an embodiment of the invention where the endoscopic image has been corner-to-corner optimized so that it covers almost both the horizontal and vertical dimension of the medical display. In certain embodiments, the endosocopic image can be optimized to cover both the horizontal and vertical dimension of the medical display.

The endoscopic image shown in FIGS. 2-4 may be automatically optimized in various embodiments of the invention. In other embodiments, the endoscopic image shown in FIGS. 2-4 may be optimized via gesture detection and/or voice control. In certain embodiments, the optimization via gesture detection and/or voice control is performed by software that picks up the voice and/or gestures exhibited by a user.

In certain embodiments, a user may pick a region of interest in the endoscopic image of the invention. In certain embodiments, a user may pick a region of interest via gesture detection and/or voice control. In certain embodiments, the user may pick a region of interest via other control methods.

Figure 5:
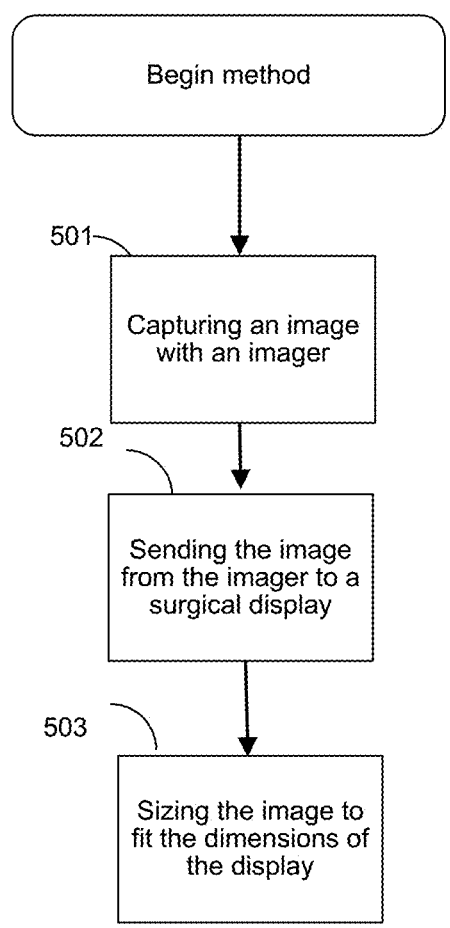
FIG. 5 is a flowchart of a method of an embodiment of the invention.
Figure 6:
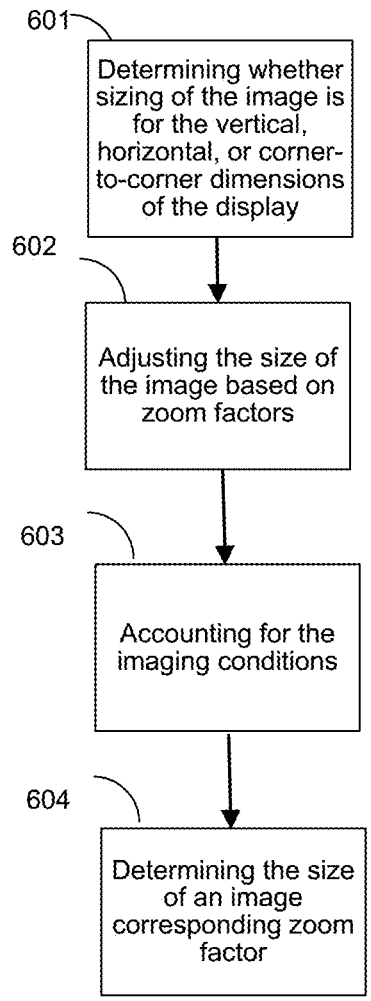
FIG. 6 is a flowchart of a various substeps in the method of FIG. 5.

FIG. 5 is a flowchart of a method of an embodiment of the invention. FIG. 5 involves capturing an image with an imager 501, sending the image from the imager to a surgical display 502 and sizing the image to fit the dimensions of the display 503. As part of this method, step 601 involves determining whether sizing of the image is for the vertical, horizontal or corner-to-corner dimensions of the display. The method involves adjusting the size of the image based on zoom factors 602, accounting for the image conditions 603 and determining the size of an image corresponding zoom factor 604. In certain embodiments, the sizing of the image is done at the display.

Figure 7:
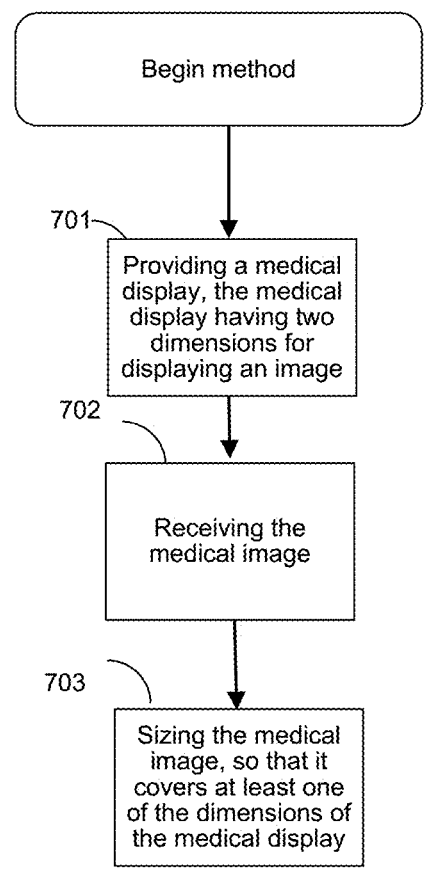
FIG. 7 is a flowchart of a method of another embodiment of the invention.

FIG. 7 is a flowchart of another method of an embodiment of the invention. FIG. 7 involves providing a medical display, the medical display having two dimensions for displaying an image 701, receiving the medical image 702 and sizing the medical image, so that it covers at least one of the dimensions of the medical display 703.

Figure 8:
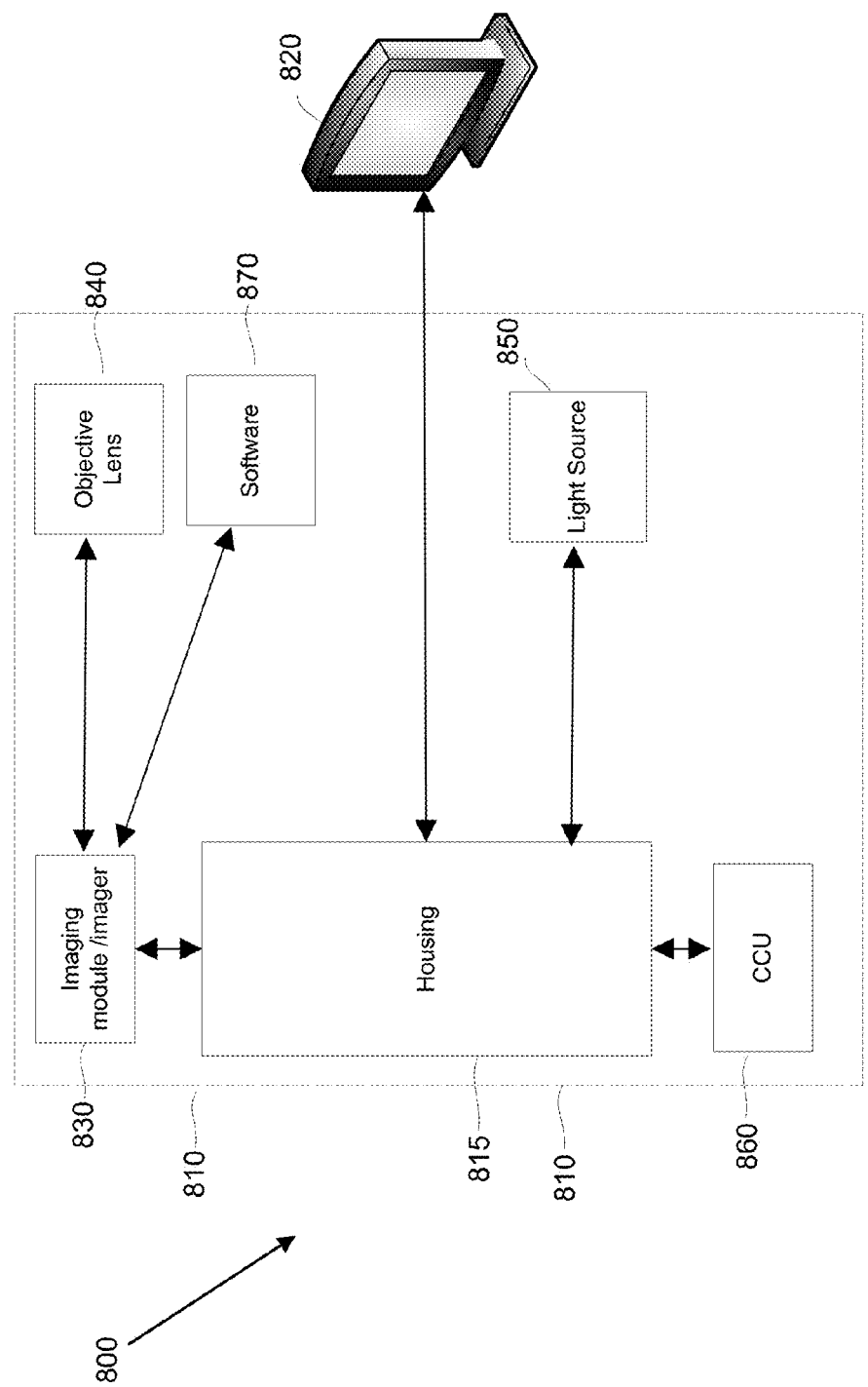
FIG. 8 shows a schematic view of another embodiment of the invention.

FIG. 8 shows an endoscopic surgical system 800. The endoscopic surgical system 800 includes an endoscope 810 and a display 820. The endoscope includes a housing 815 having an imaging module/imager 830, an objective lens 840 disposed in the imaging module 830, a light source 850, and a camera control unit 860 in communication with the imaging module 830, the camera control unit including image navigation software 870 in communication with the imager 830.

Certain embodiments of the invention includes utilizing the black mask which typically surrounds an endoscopic image to determine the proper sizing of the endoscopic image in relation to the medical display. A black mask may be produced when a camera is coupled to an endoscope ocular and the camera zoom settings (either optical, digital, or in combination) are such that a wide field of view image is rendered by the camera (see FIG. 1). Additionally, the diameter of any rod-lens image transmission system, or the diameter if a coherent fiber-optic image bundle used in flexible endoscopes will impact the diameter of the endoscopic image, and thus impact the overall size of the black mask. The endoscopic surgical system may detect a demarcation point between the endoscopic image and the black mask for adjusting the camera zoom settings to place the endoscopic image black mask demarcation point either at the vertical, horizontal, or corner-to-corner edge of the medical display, thus automatically optimizing the endoscopic image to the medical display based upon a user preference.

The invention further involves electronic circuitry and software that allows the digital and/or optical zoom to automatically optimize the image. The invention further involves various software executing on the imager to allow the digital and optical zoom to automatically optimize the image sent to the medical display.

The invention further involves electronic circuitry and software that executes on the medical display to optimize the image transmitted to the display and to zoom in and out of the image, either via digital and/or optical zoom.

The invention further involves auto-sizing of the endoscopic image to adjust the image size throughout the endoscopic case to account for changing zoom factors, endoscopes and imaging conditions.

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. A method for filling a medical display with a medical image, the method comprising the steps of:
   providing a medical display, the medical display having dimensions for displaying an image;
   receiving the medical image from an imager; and
   sizing the medical image via software executing on the medical display, the step of sizing involving:
      determining pixels of the medical display that do not have the medical image,
      determining a demarcation point between the image and the pixels that do not have the medical image, and
      optimizing, either vertically, horizontally or corner-to-corner in the medical display to fit the dimensions of the display based upon adjustment of the demarcation point either at the vertical, horizontal, or corner-to-corner edge of the medical display to fit the dimensions of the display.

2. The method of claim 1, wherein a user can select a region of interest in the medical display.

3. The method of claim 1, wherein the sizing the medical image is automatic.

4. The method of claim 1, further comprising providing image navigation software, the image navigation software executing on the medical display to perform the steps of receiving and sizing the medical image.

5. A method for sizing an endoscopic image to fit a display comprising:
   providing an endoscope, the endoscope associated with an imager;
   capturing an image with the imager;
   providing a display, the display being in communication with the imager;
   conveying the image from the imager to the display; and
   sizing the image, the step of sizing involving:
      determining pixels of the medical display that do not have the image,
      determining a demarcation point between the image and the pixels that do not have the image, and
      optimizing, either vertically, horizontally or corner-to-corner in the display to fit the dimensions of the display based upon adjustment of the demarcation point either at the vertical, horizontal, or corner-to-corner edge of the display to fit the dimensions of the display.

6. The method of claim 5, wherein the sizing of the image is automatic.

7. The method of claim 5, wherein the imager includes zoom factors and wherein the sizing of the image adjusts the zoom factors of the imager.

8. The method of claim 5, wherein the endoscopic imager is a solid state imager.

9. The method of claim 5, wherein the method is performed on an endoscopic video system, CCU, proximal camera, distal imager on a rigid endoscope, distal imager on a flexible endoscope, videoscope, and endoscope with an embedded imager.

10. The method of claim 5, wherein the sending the image from the imager to the display involves sending an electronic signal.

11. The method of claim 5, wherein the sizing of the image to fit the dimensions of the display involves software executing on the display.

12. The method of claim 5, further comprising processing the image prior to sizing the image.

13. The method of claim 5, further comprising resizing the image to adjust for changing zoom factors, endoscopes and imaging conditions.

14. An endoscopic surgical system comprising:
   an endoscope, the endoscope comprising:
      a housing having an imaging module,
      an objective lens disposed in the imaging module,
      an imager disposed in the imaging module,
      a light source, and
      a camera control unit in communication with the imaging module, the camera control unit including image navigation software in communication with the imager;
   a display; and
   software executing on the display for automatically sizing an endoscope image to fit either the vertical, horizontal, or corner-to-corner dimensions of the display, the step of sizing the endoscope image involving:
      determining pixels of the medical display that do not have the endoscope image,
      determining a demarcation point between the endoscope image and the pixels that do not have the endoscope image, and
      optimizing, either vertically, horizontally or corner-to-corner in the display to fit the dimensions of the display based upon adjustment of the demarcation point either at the vertical, horizontal, or corner-to-corner edge of the display to fit the dimensions of the display.

15. The endoscopic surgical system of claim 14, wherein the imager is disposed in the distal end of the housing.

16. The endoscopic surgical system of claim 14, wherein the imager captures a field of view.

17. The endoscopic surgical system of claim 14, wherein the objective lens is a wide-angle lens.

18. The endoscopic surgical system of claim 14, wherein the software for sizing an endoscope image involves sizing the image to fit either the vertical, horizontal, or corner-to-corner dimensions of the display.

19. The endoscopic surgical system of claim 14, wherein the software for sizing an endoscope image adjusts for changing zoom factors, endoscopes and imaging conditions.

20. The endoscopic surgical system of claim 14, wherein the software for sizing the image adjusts for imaging conditions.

21. A method for sizing an endoscopic image to fit a surgical display comprising:
   providing an imager;
   capturing an image with said imager;
   conveying the image from the imager to a surgical display in communication with the imager;
   automatically sizing the captured image to fit either the vertical, horizontal, or corner-to-corner dimensions of the surgical display, the sizing of the image involving
      determining pixels of the surgical display that do not have the image,
      determining a demarcation point between the image and the pixels that do not have the medical image, and
      optimizing, either vertically, horizontally or corner-to-corner in the surgical display to fit the dimensions of the surgical display based upon adjustment of the demarcation point either at the vertical, horizontal, or corner-to-corner edge of the surgical display to fit the dimensions of the surgical display, adjusting the image size to account for changing zoom factors, endoscope and imaging conditions, wherein the captured image is vertically optimized, horizontally optimized or corner-to-corner optimized in the surgical display.

22. The method of claim 21, wherein the automatic sizing the captured image adjusts for magnification factors used to capture the captured image.

* * * * *